United States Patent
Sharko

(10) Patent No.: US 9,828,565 B2
(45) Date of Patent: Nov. 28, 2017

(54) ALCOHOL COMPOSITION AND DERIVATIVES THEREOF

(71) Applicant: SHELL OIL COMPANY, Houston, TX (US)

(72) Inventor: Paul Theodore Sharko, Houston, TX (US)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 15/384,347

(22) Filed: Dec. 20, 2016

(65) Prior Publication Data

US 2017/0175026 A1    Jun. 22, 2017

Related U.S. Application Data

(60) Provisional application No. 62/270,615, filed on Dec. 22, 2015.

(51) Int. Cl.

| | | |
|---|---|---|
| *C10M 173/02* | (2006.01) | |
| *C07F 5/04* | (2006.01) | |
| *C07C 29/16* | (2006.01) | |
| *C07C 27/00* | (2006.01) | |
| *C10M 135/08* | (2006.01) | |
| *C11D 11/00* | (2006.01) | |
| *C10M 105/14* | (2006.01) | |
| *C10M 133/04* | (2006.01) | |
| *B01F 17/00* | (2006.01) | |
| *C11D 1/04* | (2006.01) | |
| *C11D 1/14* | (2006.01) | |
| *C11D 1/29* | (2006.01) | |
| *C11D 1/44* | (2006.01) | |
| *C11D 3/20* | (2006.01) | |

(52) U.S. Cl.
CPC ....... *C10M 135/08* (2013.01); *B01F 17/0021* (2013.01); *C10M 105/14* (2013.01); *C10M 133/04* (2013.01); *C11D 1/04* (2013.01); *C11D 1/146* (2013.01); *C11D 1/29* (2013.01); *C11D 1/44* (2013.01); *C11D 3/2017* (2013.01); *C11D 3/2093* (2013.01); *C11D 11/0017* (2013.01); *C10M 2207/021* (2013.01); *C10M 2215/02* (2013.01); *C10M 2219/042* (2013.01)

(58) Field of Classification Search
CPC .......... C10M 2219/044; C07C 29/32
USPC .......... 508/200, 389; 568/883, 902
See application file for complete search history.

(56) References Cited

U.S. PATENT DOCUMENTS

| | | |
|---|---|---|
| 3,231,621 A | 1/1966 | Slaugh et al. |
| 3,239,566 A | 3/1966 | Slaugh et al. |
| 3,239,569 A | 3/1966 | Slaugh et al. |
| 3,239,570 A | 3/1966 | Slaugh et al. |
| 3,239,571 A | 3/1966 | Slaugh et al. |
| 3,420,898 A | 1/1969 | Van Winkle et al. |
| 3,440,291 A | 4/1969 | Van Winkle et al. |
| 3,448,157 A | 6/1969 | Slaugh et al. |
| 3,448,158 A | 6/1969 | Slaugh et al. |
| 3,480,556 A * | 11/1969 | Witt ............ C11D 1/146 510/428 |
| 3,496,203 A | 2/1970 | Morris et al. |
| 3,496,204 A | 2/1970 | Morris et al. |
| 3,501,515 A | 3/1970 | Van Winkle et al. |
| 4,322,545 A | 3/1982 | Scala, Jr. |
| 5,072,057 A | 12/1991 | Oswald et al. |
| 7,183,446 B2 | 2/2007 | Zeller et al. |
| 2004/0030200 A1 * | 2/2004 | Zeller ............ C07C 29/16 568/876 |
| 2006/0247148 A1 * | 11/2006 | Ortiz ............ C11D 1/37 510/424 |

FOREIGN PATENT DOCUMENTS

WO    9823566    6/1998

OTHER PUBLICATIONS

Zoller et al.; "Detergents Part F: Production"; CRC Press; p. 24; 2009.

* cited by examiner

*Primary Examiner* — Vishal Vasisth

(57) ABSTRACT

The invention provides a composition comprising a mixture of tridecanols wherein at least about 60 wt % of the mixture is linear tridecanol and at least about 10 wt % of the mixture is branched tridecanols wherein the branched tridecanols have branching on the second carbon atom. The mixture of tridecanols may be converted to one or more derivatives, and these derivatives may be used in laundry detergents, cleaning products or as an agricultural adjuvant, an emulsifying agent, a lubricant additive, a pour point depressant, or a personal care ingredient.

16 Claims, No Drawings

ALCOHOL COMPOSITION AND DERIVATIVES THEREOF

The present application claims the benefit of U.S. Provisional Patent Application Ser. No. 62/270,615, filed Dec. 22, 2015.

FIELD OF THE INVENTION

The present invention relates to an alcohol composition comprising tridecanols and derivatives thereof.

BACKGROUND OF THE INVENTION

Primary tridecanols are well known and commonly used to synthesize plasticizers and surface active agents. The most common tridecanol alcohol is a completely branched alcohol known as tridecyl alcohol or isotridecanol. Tridecyl alcohol is most commonly produced by tetramerizing propylene and performing the oxo hydroformylation reaction as described in *Industrial Organic Chemicals*; Wittcoff, Harold A., Reuben, Bryan G., and Plotkin, Jeffrey S., Wiley-Interscience, 2013 p. 221. This type of alcohol is marketed by ExxonMobil as EXXAL 13. A second type of primary tridecanol is produced by performing the oxo hydroformylation reaction on a linear dodecene as disclosed in U.S. Pat. No. 7,183,446. This yields a tridecanol containing 40% or greater of branched species.

While both types of tridecanol can be used to synthesize useful derivatives like plasticizers and surface active agents, the high degree of branching limits the functionality of these derivatives. There is a need for a tridecanol with a lower proportion of branched species.

SUMMARY OF THE INVENTION

The invention provides a composition comprising a mixture of tridecanols wherein at least about 60 wt % of the mixture is linear tridecanol and at least about 10 wt % of the mixture is branched tridecanols wherein the branched tridecanols have branching on the second carbon atom.

The mixture of tridecanols may be converted to one or more derivatives, and these derivatives may be used in laundry detergents, cleaning products or as an agricultural adjuvant, an emulsifying agent, a lubricant additive, a pour point depressant, or a personal care ingredient.

DETAILED DESCRIPTION

The present invention provides a tridecanol with a low degree of branching and derivatives made therefrom. The more elongated and less bulky molecular character of this tridecanol confers superior characteristics to derivatives derived from it. This is particularly apparent in plasticizer and surface active agent derivatives. Plasticizer derivatives made with this tridecanol are expected to exhibit less volatility, more resistance to environmental damage, and superior response to temperature extremes in use, when compared to similar plasticizers produced with more highly branched tridecanols. Surface active agents made with this tridecanol are expected to exhibit better detergency and soil adsorption than similar surface active agents made with more highly branched tridecanols. In addition they are likely to be more readily biodegraded in the environment.

The present invention provides a mixture of primary tridecanols wherein at least about 60 wt % of the mixture is linear tridecanol and at least about 10 wt % of the mixture is branched tridecanols wherein the branched tridecanols have branching on the second carbon atom. The mixture may contain at least about 70 wt % linear tridecanols. The mixture may contain at least about 15 wt % branched tridecanols.

The derivatives of the tridecanols include esters of dicarboxylic acids or other polyacids useful as plasticizers as well as alkoxylated alcohols, sulfated alcohols, sulfated alkoxylated alcohols, alcohol ether amines, or other derivatives with hydrophilic moieties useful as surface active agents. Linear tridecanols have the structure (1):

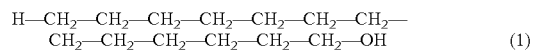

(1)

Branched tridecanols have the general structure (2):

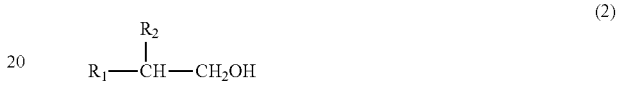

(2)

where $R_1$ and $R_2$ are linear alkyl chains containing a total of 11 carbon atoms in the two alkyl chains.

Mixtures having the composition of approximately 60-90 wt % of structure (1) and 10-40 wt % of structure (2) can be synthesized from linear dodecene by the modified Oxo process, using a phosphine, phosphite, arsine, or pyridine ligand modified cobalt or rhodium catalyst, as described in U.S. Pat. Nos. 3,231,621, 3,239,566, 3,239,569, 3,239,570, 3,239,571, 3,420,898, 3,440,291, 3,448,158, 3,448,157, 3,496,203, 3,496,204, 3,501,515 and 3,527,818, the disclosures of which are incorporated herein by reference.

Hydroformylation denotes the reaction of an olefin with CO and $H_2$ to produce an aldehyde/alcohol which has one more carbon atom than the reactant olefin. The term hydroformylation may also cover the step of forming an aldehyde and the subsequent reduction to the alcohol. As used herein, hydroformylation refers to the production of alcohols from olefins via carbonylation and an aldehyde reduction process.

Alcohol derivatives useful as plasticizers are well known in the art. Synthesis and properties of common plasticizers are disclosed in *Technology of Plasticizers*; Sears, J. Kern and Darby, Joseph R., John Wiley & Sons, 1982, p. 16 and references cited therein. The present invention includes plasticizers synthesized from a mixture of primary tridecanols in which at least about 60 wt % of the alkyl chains are linear and at least about 10 wt % of the alkyl chains are branched at the 2-carbon position.

A preferred embodiment of this invention is diesters of the tridecanol mixture with diacids. Common diacids that can be esterified to produce plasticizers include phthalic acid, adipic acid, sebacic acid, terephthalic acid, and succinic acid. An additional preferred embodiment of this invention includes polyesters of polyacids containing three or more acid moieties. One polyacid that can be esterified to produce plasticizers is trimellitic acid.

Alcohol derivatives useful as surface active agents are well known in the art. Synthesis and properties of common surface active agents are disclosed in *Handbook of Detergents Part F: Production*, Zoller, Uri and Sosis, Paul CRC Press, 2009, p. 24 and references cited therein.

The present invention includes surface active agents synthesized from a mixture of primary tridecanols in which at least about 60 wt % of the alkyl chains are linear and at least about 10 wt % of the alkyl chains are branched at the 2-carbon position. Preferred embodiments of this invention include polyalkoxylates, sulfates, sulfated polyalkoxylates, and ether amines of the novel tridecanol mixture.

U.S. Pat. No. 3,440,291 describes the hydroformylation of linear 1-dodecene to form mixtures of branched and linear tridecanols. This mixture could be separated by partial crystallization or other methods into several fractions of different concentrations of branched and linear species. By combining these fractions, several samples of tridecanol mixtures with specified ratios of branched/linear ratios could then be prepared. The branching of samples (1-4) that could be made is shown in Table 1.

TABLE 1

| Sample | Branch to Linear Ratio |
|---|---|
| 1 | 10:90 |
| 2 | 20:80 |
| 3 | 40:60 |
| 4 | 60:40 |

Plasticizer Applications

The use of tridecanols in plasticizer applications is well known in the art. Particularly well known are diesters of phthalic anhydride (di-tridecyl phthalate) and triesters of trimellitic acid (tri-tridecyl trimelletate). For example, the diester of EXXAL 13 and phthalic anhydride is sold by ExxonMobil Corporation under the trade name JAYFLEX DTDP. It is well known for its low rate of migration at elevated temperature.

Diesters of the alcohols in Samples 1-4 with phthalic anhydride could be prepared and each incorporated into a standard grade of PVC. These samples could then be compared to a sample of PVC plasticized with DOP (di-2-ethylhexyl phthalate). Rate of loss on heating was measured on each sample of plasticized PVC at 50° C. It is expected that the 4 samples and a diester made with EXXAL 13 would all show a significantly lower rate of loss compared with the sample containing DOP. Among the PVC samples, the rate of loss would be expected to decrease as the degree of branching decreases. The lowest rate of loss should be observed from the PVC sample plasticized with the diester of the alcohol in Sample 1 with phthalic anhydride.

Household Detergent Applications

Alcohols in the range from C12 to C16 are often referred to as detergent alcohols due to the many derivatives that find use as detergent products. In these applications an important property is the rate at which the alcohol biodegrades under aerobic conditions. If an organic chemical biodegrades to a 60% level in 28 days it is considered "readily biodegradable." The alcohol samples 1-4 should be readily biodegradable, but the EXXAL 13 likely is not. This alcohol will not be considered further as a detergent alcohol.

Detergent derivatives of alcohols in the C12 to C16 range have many properties that depend on the length of the carbon chain. In soaps, carboxylate derivatives of alcohols from C12 to C14 are known for their high rate of lather and degree of solubility. Carboxylate derivatives from C15 to C16 are known for their low rate of lather and low solubility. Of these the carboxylate derivatives from C12 to C14, it is known that lathering decreases from C12 to C14 but skin irritation potential also decreases similarly. C13 carboxylates are expected to offer a good balance between lathering and skin irritation potential.

Alcohol sulfate surfactants in the C12 to C16 range are often used in dishwashing products. Similarly to the carboxylates, C12 alcohol sulfates are known to offer the best flash foam but are also the harshest to the skin. C14 alcohol sulfates are known to not foam as much but are milder. C13 alcohol sulfates are expected to offer a good balance between foaming and skin mildness. This trend is seen in many other classes of surfactant. If choosing between a C12 derivative and a C14 derivative, often the C13 derivative would provide a good compromise.

The presence of low levels of branching provides a benefit to handling the alcohol in processing. The higher the branching content, the lower the pour point, affording ease and economy in processing. Branching in alcohol derivatives also show benefits. In alcohol sulfates, branching raises the Krafft point resulting in greater solubility and a broader effective temperature range. On the opposite hand, soil removal properties are often impacted negatively by high degrees of branching. We find that alcohols having 10-40% branching provide an optimal tradeoff between low temperature solubility and soil removal for many surfactant derivatives.

Similar results are expected for other derivatives including carboxylate, sulfate, alkoxylate, and alkoxylate sulfate derivatives. In most cases the range of preferred properties would be demonstrated when the hydrophobe is C13 and the branching level is 10% to 40%. We would expect to see similar results in other classes of surfactants not mentioned here. Additionally we anticipate other useful derivative mixtures could be used as an agricultural adjuvant, an emulsifying agent, a lubricant additive, a pour point depressant, or a personal care ingredient.

The invention claimed is:

1. A composition comprising a mixture of tridecanols wherein at least about 60 wt % of the mixture is linear tridecanol and at least about 10 wt % of the mixture is branched tridecanols wherein the branched tridecanols have branching on the second carbon atom.

2. The composition of claim 1 wherein at least about 70 wt % of the mixture is linear tridecanol.

3. The composition of claim 1 wherein at least about 15 wt % of the mixture if branched tridecanols.

4. A composition comprising one or more derivatives of the tridecanol mixture as claimed in claim 1.

5. The composition of claim 4 wherein the derivatives comprise esters of dicarboxylic acids, esters of polycarboxylic acids, alkoxylated alcohols, sulfated alcohols, sulfated alkoxylated alcohols and alcohol ether amines.

6. The composition of claim 4 wherein the derivative comprises a diester of the tridecanol mixture with one or more diacids.

7. The composition of claim 6 wherein the diacids comprise phthalic acid, adipic acid, sebacic acid and succinic acid.

8. The composition of claim 4 wherein the derivative comprises a polyester of the tridecanol mixture with one or more polyacids.

9. The composition of claim 8 wherein the polyacid comprises trimellitic acid.

10. The composition of claim 4 wherein the derivatives comprise a polyalkoxylate, sulfate, sulfated polyalkoxylate or ether amine.

11. A hard surface cleaning formulation comprising the composition of claim 10.

12. A laundry detergent formulation comprising the composition of claim 10.

13. The use of the composition of claim 4 as an agricultural adjuvant, an emulsifying agent, a lubricant additive, a pour point depressant, or a personal care ingredient.

14. The composition of claim 1 wherein at least about 65 wt % of the mixture is linear tridecanol and at least about 15 wt % of the mixture is branched tridecanols.

15. The composition of claim 1 wherein from 60-80 wt % of the mixture is linear tridecanol.

16. The composition of claim 1 wherein from 10-25 wt % of the mixture is branched tridecanols.

\* \* \* \* \*